United States Patent [19]
Stirnadel et al.

[11] Patent Number: 4,946,682

[45] Date of Patent: Aug. 7, 1990

[54] MEDICATION CONTAINING EXTRACT SUBSTANCES FROM PLANTS OR PLANT PARTS OF THE SPECIES LEPTOSPERMUM SCOPARIUM

[75] Inventors: Alfred Stirnadel, Zweibrucker Strasse 63, D-6660 Zweibrucken 15; Ute H. Stirnadel, Zweibrucken, both of Fed. Rep. of Germany

[73] Assignee: Alfred Stirnadel, Zweibrucken, Fed. Rep. of Germany

[21] Appl. No.: 304,932

[22] Filed: Feb. 1, 1989

Related U.S. Application Data

[63] Continuation of Ser. No. 105,450, Oct. 5, 1987, abandoned, which is a continuation of Ser. No. 775,401, Sep. 12, 1985, abandoned.

[30] Foreign Application Priority Data

Aug. 2, 1985 [EP] European Pat. Off. ........ 85109771.3

[51] Int. Cl.$^5$ ............................................. A61K 35/78

[52] U.S. Cl. ................................................. 424/195.1

[58] Field of Search ..................................... 424/195.1

[56] References Cited

PUBLICATIONS

Cancer Chemo. Screening Data, Can. Res. Sup 27:113, 1967.
Lewis, Med. Bot. pp. 132–135, 1977.
Chem 92: 143231m, 1980.
Chem Absts., 87: 1906c, 1977.

*Primary Examiner*—John W. Rollins
*Attorney, Agent, or Firm*—Burns, Doane, Swecker & Mathis

[57] ABSTRACT

Active substance extracts obtained through extraction or steam distillation of leaves, stems and blossoms of the plant specie *Leptospermum Scoparium* are suited for the treatment of degenerative phenomena of the organism, such as arthritis, or suitable for treating tumors, leukemia and multiple sclerosis.

5 Claims, No Drawings

MEDICATION CONTAINING EXTRACT SUBSTANCES FROM PLANTS OR PLANT PARTS OF THE SPECIES LEPTOSPERMUM SCOPARIUM

This application is a continuation of application Ser. No. 07/105,450, filed Oct. 5, 1987, now abandoned, in turn a continuation of Ser. No. 775,401, filed Sept. 12, 1985 now abandoned.

BACKGROUND OF THE INVENTION

The present invention relates to extracts of plants which are useful as medications.

Extracted substances from plant material, such as leaves, blossoms and fruits, have always been used to treat diverse illnesses. The active substances contained in these plants may be obtained via extraction from the plant parts using water, alcohol or other organic solutions or mixtures thereof, or by using steam heat distillation.

SUMMARY OF THE INVENTION

The present invention is a composition which comprises an extract of the specie *Leptospermum scoparium*.

DETAILED DESCRIPTION OF THE INVENTION

Surprisingly, it now has been established that plants of the type *Leptospermum scoparium*, which belong to the Myrtaceae family, contain in their blossoms, buds, leaves and stems, active substances, mainly in the form of ethereal oils. In that form and in relatively small amounts, these oils are already suitable for oral application as a remedy for degenerative phenomena such as arthritis or treatment of tumors, leukemia and multiple sclerosis.

As stated above, the subject of this invention is a medication which contains extract substances from plants or plant parts of the type *Leptospermum scoparium*.

These extracts or active substances apparently activate the natural resistance of the organism against degenerative processes or cancerous phenomena in the body. This newly recognized effect is even more surprising, since the professional world has experimented with all kinds of plants and plant parts for hundreds of years, testing them for substances which could have a therapeutic effect, and plants of the *Leptospermum scoparium* family are well known. *Leptospermum scoparium* grows in Australia and New Zealand, and is admired in Europe for its red or pink blossoms.

Preferably the drug should contain extract substances from the *Leptospermum scoparium* type. The hybrids are obtained through mutation or hybridization. Some of the hybrid types commercially available are:

| | |
|---|---|
| BALLERINA | GAITY GIRL |
| BIG RED | JUBILEE |
| BLOSSOM | PINK PEARL |
| BURGUNDY QUEEN | SPECTRECOLOUR |
| FANTASIA | SUNRAYSIA |
| CHERRY RIPE | WINTER CHEER |
| CORAL CANDY | CRIMSON GLORY |

For the manufacture of the drug, crushed or ground leaves, stems and/or blossoms or *Leptospermum scoparium* are mixed with ethanol or aqueous ethanol. After separating the plant parts, the extract is diluted to the desired concentration. Preferably, the plant material should be used just prior to full bloom. Plant parts are shredded or cut up without the roots, and the extract is extracted with ethanol or aqueous ethanol, particularly with 43% ethanol and heat, preferably through heating under reflux, a procedure well known. The fresh or carefully dried, cut up plants or parts of plants, without the roots, may be put to use in this manner.

Another type of procedure to manufacture the drug is as follows: the substances to be extracted from the base material are obtained through steam heat distillation and result in an ethereal oil.

The obtained decoctum, either as an alcoholic or aqueous alcoholic extract can then be applied directly in any desired diluted form. Due to the high activity of the extract substances from *Leptospermum scoparium*, the extract is particularly suitable for application in homoeopathic dilution according to the guidelines governing homoeopathic medicine books. Especially according to regulation 19e in an application of D1-D6 potency, the drops are generally to be taken 3 times daily, 5 to 15/25 drops just before a meal. This corresponds to 1-4 ml/day for each 70 kg of body weight.

The basic infusion can be utilized in oral application as a phytopharmacon to be used direct as is, or diluted at a 1:10 ratio with 30% ethanol or in a 1% salt solution. In this case, 10 to 25 drops are recommended on a daily basis.

In order to further illustrate the present invention and the advantages thereof, the following specific examples are given, it being understood that these examples are intended only to be illustrative without serving as a limitation on the scope of the present invention.

EXAMPLE 1

200 g of freshly harvested leaves with thin stems, of the hybrid specie *Leptospermum scoparium* are cut into small pieces, and are mixed with 600 g 43% aqueous ethanol. The mixture is heated to a simmering boil and is kept 30 minutes under reflux. After cooling, the mixture is kept sealed for 24 hours, whereupon the extract solution obtained is separated and cleaned by pressing and filtering the same.

The extract obtained can be used for application either undiluted or diluted with 30% ethanol in 1:10 or 1:100 ratio. Appropriately, 20 drops of this diluted extract are taken orally. This is 3 to 4 ml each day per 70 kg of body weight. If dilution is desired according to the rules of homoeopathy, 3 parts of the filtered extracts should be mixed with 7 parts of 30% ethanol, whereupon this first decimal dilution (D1) is again diluted using 15%-30% ethanol, ratio 1:9.

The dilution so obtained (D2) may then be used for oral treatment of a leukemia patient, or may be diluted further.

EXAMPLE 2

100 g of dried and ground plant material (stems and leaves) of hybrid type Leptospermum scoparium is mixed with 1 liter of 43% ethanol under reflux, as described in Example 1. After cooling and letting the mixture stand for 24 hours, it is pressed and filtered.

As the obtained extract now already corresponds to a D1 dilution, to obtain a D2 dilution the extract is again mixed with 30% ethanol, using a 1:9 parts ratio. If desired, 1 part of the so obtained solution is again mixed with 9 parts of 15% ethanol, resulting in a third decimal dilution. The dilutions obtained in this manner (potency D1-D3) can be administered to the patient orally.

With consistent application, the diluted extracts from *Leptospermum scoparium* hybrids show visible results in 3 to 6 weeks. The medicine has no adverse effects, especially in the concentrated forms mentioned. There is no detrimental effect upon the stomach or digestive tract.

EXAMPLE 3

The ethereal oil, obtained via distillation from plant parts of the *Leptospermum scoparium* hybrids, may be diluted with ethanol or olive oil in ratios 1:10, 1:100, and 1:10 000, and can then be applied as follows:

3 times 3-5 drops, or 3 times 15-20 drops.

While the invention has been described in terms of various preferred embodiments, one skilled in the art will appreciate that various modifications, substitutions, omissions, and changes may be made without departing from the spirit thereof. Accordingly, it is intended that the scope of the present invention be limited solely by the scope of the following claims.

What is claimed is:

1. A pharmaceutical composition comprising an extract of the leaves, stems or blossoms of a hybrid of the specie *Leptospermum scoparium*, wherein the hybrid is Ballerina, Big Red, Blossom, Burgundy Queen, Fantasia, Cherry Ripe, Coral Candy, Gaity Girl, Jubilee, Pink Pearl, Spectrecolour, Sunraysia, Winter Cheer, or Crimson Glory.

2. The pharmaceutical composition according to claim 1 wherein the hybrid is Ballerina, Burqundy Queen, or Crimson Glory.

3. A process for preparing the pharmaceutical composition of claim 1 comprising cutting up the leaves, stems or blossoms; mixing the cut-up leaves, stems or blossoms with an extractant selected from the group consisting of ethanol and aqueous ethanol; and extracting the leaves, stems or blossoms under heating to reflux; separating the leaves, stems or blossoms to obtain an extract; and diluting the extract to the desired concentration.

4. The process of claim 3 wherein the extract is obtained as an ethereal oil through steam heat distillation.

5. A method for the treatment of an leukemia and tumors in mammals comprising oral administration to the mammal of an effective amount of an extract of the leaves, stems or blossoms of a hybrid of the specie *Leptospermum scoparium*, wherein the hybrid is Ballerina, Big Red, Blossom, Burgundy Queen, Fantasia, Cherry Ripe, Coral Candy, Gaity Girl, Jubilee, Pink Pearl, Spectrecolour, Sunraysia, Winter Cheer, or Crimson Glory wherein the leukemia and tumors are sensitive to treatment with the extract.

* * * * *